(12) United States Patent
Allais et al.

(10) Patent No.: US 8,975,432 B2
(45) Date of Patent: Mar. 10, 2015

(54) PROCESS FOR PREPARING ALKANEDIOL AND DIALKYL CARBONATE

(75) Inventors: Cyrille Paul Allais, Amsterdam (NL); Timothy Michael Nisbet, Amsterdam (NL); Garo Garbis Vaporciyan, Houston, TX (US); Cornelis Leonardus Maria Vrouwenvelder, Amsterdam (NL)

(73) Assignee: Shell Oil Company, Houston, TX (US)

( * ) Notice: Subject to any disclaimer, the term of this patent is extended or adjusted under 35 U.S.C. 154(b) by 272 days.

(21) Appl. No.: 13/509,648

(22) PCT Filed: Nov. 15, 2010

(86) PCT No.: PCT/EP2010/067464
§ 371 (c)(1),
(2), (4) Date: Oct. 16, 2012

(87) PCT Pub. No.: WO2011/058168
PCT Pub. Date: May 19, 2011

(65) Prior Publication Data
US 2013/0066099 A1    Mar. 14, 2013

(30) Foreign Application Priority Data

Nov. 16, 2009 (EP) ................................. 09176135

(51) Int. Cl.
*C07C 68/06* (2006.01)
*C07C 29/48* (2006.01)

(52) U.S. Cl.
CPC .................................... *C07C 68/065* (2013.01)
USPC ......................................... 558/274; 558/277

(58) Field of Classification Search
None
See application file for complete search history.

(56) References Cited

U.S. PATENT DOCUMENTS

| 3,642,858 | A | 2/1972 | Frevel et al. |
| 3,803,201 | A | 4/1974 | Gilpin et al. ................... 260/463 |
| 4,062,884 | A | 12/1977 | Ramano et al. ............... 260/463 |
| 4,508,927 | A | 4/1985 | Bhise et al. .................... 568/858 |
| 4,691,041 | A | 9/1987 | Duranleau et al. ............ 558/277 |
| 5,359,118 | A | 10/1994 | Wagner et al. ................ 558/277 |
| 5,508,442 | A | 4/1996 | Wagner et al. ................ 549/228 |

FOREIGN PATENT DOCUMENTS

| CN | 1128664 | 8/1996 | |
| CN | 1946660 | 4/2007 | |
| EP | 001082 | 3/1979 | ............. C07C 69/96 |
| EP | 180387 | 5/1986 | .......... C07D 301/02 |
| EP | 274953 | 7/1988 | ............. C07C 69/96 |
| EP | 1760059 | 12/2005 | ............. C07C 27/02 |
| JP | 2002371037 | 12/2002 | ............. C07C 68/08 |
| JP | 2003300917 | 10/2003 | ............. C07C 27/02 |
| WO | WO2008090108 | 7/2008 | ............. C07C 68/06 |

OTHER PUBLICATIONS

Machine translation of JP 2003-300917, obtained from <http://worldwide.espacenet.com/>, Accessed Feb. 23, 2014.*
Knifton, J. F. et al., "Ethylene Glycol-Dimethyl Carbonate Cogeneration", Journal of Molecular Catalysis, vol. 67 (1991) pp. 389-399.

* cited by examiner

*Primary Examiner* — Alicia L Otton

(57) ABSTRACT

The invention relates to a process for the preparation of an alkanediol and a dialkyl carbonate comprising:
reacting an alkylene carbonate and an alkanol in the presence of a transesterification catalyst to obtain a reaction mixture comprising dialkyl carbonate, unconverted alkanol, alkanediol, unconverted alkylene carbonate and an alkoxy alkanol impurity; and
subjecting the reaction mixture to distillation in a series of steps.

6 Claims, 1 Drawing Sheet

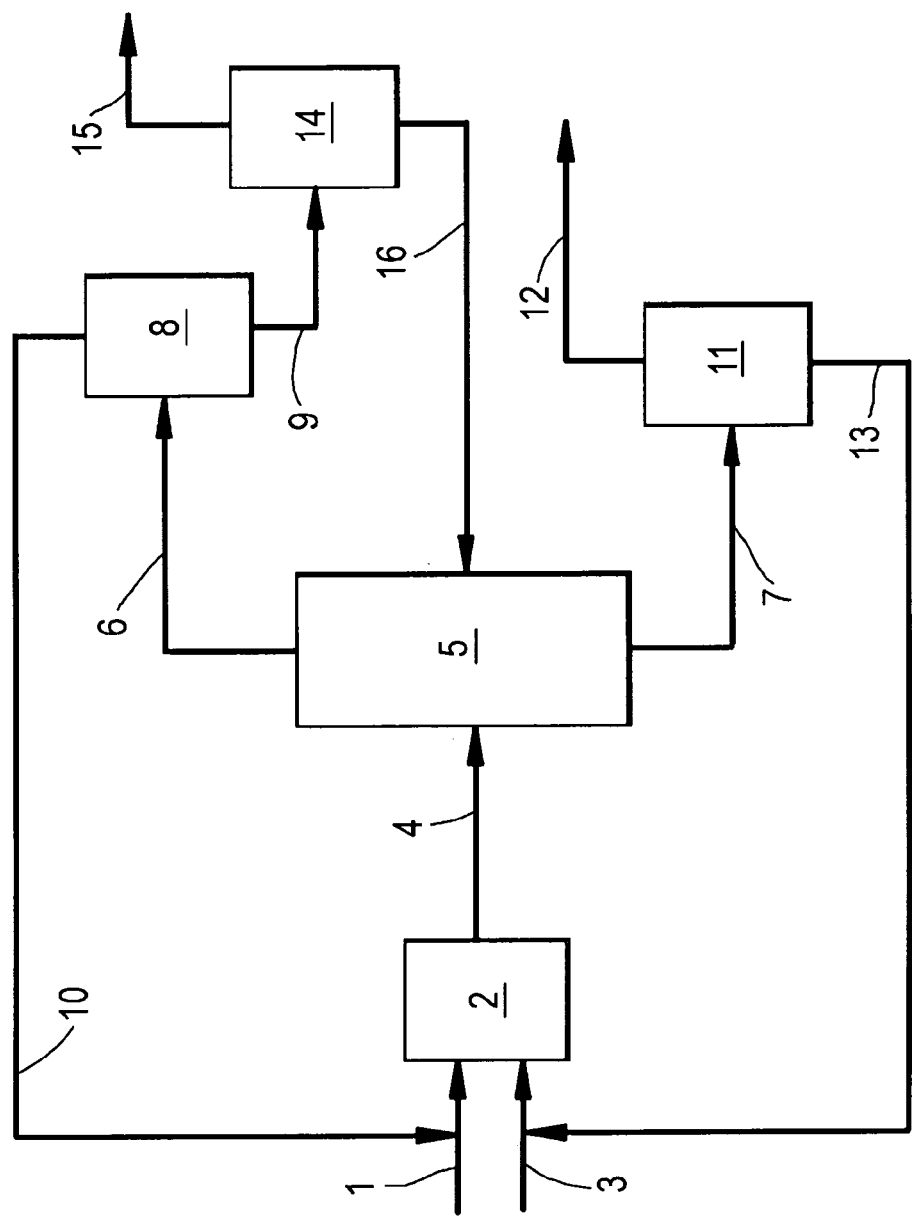

PROCESS FOR PREPARING ALKANEDIOL AND DIALKYL CARBONATE

PRIORITY CLAIM

The present application claims priority from PCT/EP2010/067464, filed 15 Nov. 2010, which claims priority from EP 09176135.3, filed 16 Nov. 2009.

FIELD OF THE INVENTION

The present invention relates to a process for the preparation of an alkanediol and a dialkyl carbonate from an alkylene carbonate and an alkanol.

BACKGROUND

Such transesterification process is for example disclosed in WO2008090108, which discloses a process for recovering dialkyl carbonate from a reaction mixture obtained from reacting an alkylene carbonate and an alkanol. It has been found that in the dialkyl carbonate produced and separated in the way as described in WO2008090108, an alkoxy alkanol impurity may be present. For example, in a process where ethylene carbonate is reacted with ethanol, the products are diethyl carbonate and monoethylene glycol. However, in such process, 2-ethoxyethanol may also be formed and end up in the diethyl carbonate as an impurity.

In addition, JP2003300917 and JP2002371037 relate to processes wherein dimethyl carbonate and monoethylene glycol are made from ethylene carbonate and methanol and wherein 2-methoxyethanol is formed as a by-product, which is also an alkoxy alkanol. In the inventions of JP2003300917 and JP2002371037, said 2-methoxyethanol can be removed by specific distillation techniques.

Within the process producing an alkanediol and a dialkyl carbonate from an alkylene carbonate and an alkanol, the alkoxy alkanol impurity may be formed in various ways. For example, in a reactor where ethanol and ethylene carbonate are reacted into diethyl carbonate and monoethylene glycol, a side-reaction of ethanol with ethylene oxide, formed by back-reaction of ethylene carbonate into ethylene oxide and carbon dioxide, into 2-ethoxyethanol (ethyl oxitol) may take place. Further, ethyl oxitol may be formed by a side-reaction of ethanol with ethylene carbonate in such a way that carbon dioxide is released and ethyl oxitol is produced. Still further, a side-reaction between ethanol and monoethylene glycol may take place producing ethyl oxitol and water. Still even further, ethyl oxitol may be formed via decarboxylation of hydroxyethyl ethyl carbonate.

Therefore, the product stream from a reactor where ethanol and ethylene carbonate are reacted into diethyl carbonate and monoethylene glycol, may comprise unconverted ethanol, unconverted ethylene carbonate, diethyl carbonate, monoethylene glycol and the above-mentioned ethyl oxitol impurity. The presence of said alkoxy alkanol impurity may be detrimental in any subsequent production process. Said alkoxy alkanol impurity may for example end up in the dialkyl carbonate that is used as a starting material for the synthesis of diphenyl carbonate from said dialkyl carbonate and phenol. For example, in a case where the dialkyl carbonate is diethyl carbonate and the alkoxy alkanol impurity is ethyl oxitol, said ethyl oxitol may react with the phenol starting material and/or with the diphenyl carbonate product.

Direct reaction of phenol and ethyl oxitol may result in the production of phenyl 2-ethoxyethyl ether, and hence in the loss of valuable phenol reactant. Further, such reaction results in the introduction of undesired chemicals in the process and therefore to separation issues.

Reaction of diphenyl carbonate with ethyl oxitol results in product loss as phenyl 2-ethoxyethyl carbonate is produced. Further, the latter product acts as a "poison" in any subsequent polymerisation of diphenyl carbonate into polycarbonate material. For example, when diphenyl carbonate is reacted with bis-phenol A (BPA), polycarbonate and phenol are formed. Diphenyl carbonate can react with BPA since phenol is a relatively good leaving group. Dialkyl carbonates (such as diethyl carbonate) however cannot be used to produce polycarbonate by reaction with BPA, since alkanols are not good leaving groups. Alkoxy alkanols (such as ethyl oxitol) are neither good leaving groups. Therefore, in case phenyl 2-ethoxyethyl carbonate is present in a diphenyl carbonate feed to be reacted with BPA, phenol will be released easily from said phenyl 2-ethoxyethyl carbonate but not ethyl oxitol which will consequently stop the polymerization process at one end of the chain. Consequently, phenyl 2-ethoxyethyl carbonate should be removed from diphenyl carbonate before the latter is contacted with BPA.

The above exemplifies that in a case where a dialkyl carbonate stream containing an alkoxy alkanol impurity is formed, it is desired to remove said alkoxy alkanol impurity before any subsequent process takes place wherein the dialkyl carbonate is transformed into a valuable end product. For example, it is desirable to remove any ethyl oxitol impurity from a diethyl carbonate stream containing said impurity before reaction of the diethyl carbonate with phenol takes place.

Referring to the above example where ethanol and ethylene carbonate have been reacted into diethyl carbonate and monoethylene glycol, the product stream also containing unconverted ethanol and ethylene carbonate and ethyl oxitol side-product, may be separated by means of distillation. The boiling points for the various components in said product stream are mentioned in the table below.

| Component | Boiling point (° C.) |
| --- | --- |
| ethanol | 78.4 |
| diethyl carbonate | 126-128 |
| ethyl oxitol | 135 |
| monoethylene glycol | 197.3 |
| ethylene carbonate | 260.4 |

The distillation as referred to above may result in a top stream containing diethyl carbonate and unconverted ethanol and a bottom stream containing monoethylene glycol and unconverted ethylene carbonate. Ethyl oxitol may end up in said top stream as an impurity. Subsequently, said top stream may be further separated by means of distillation into a top stream containing unconverted ethanol which can be recycled to the reactor where diethyl carbonate and monoethylene glycol are produced, and a bottom stream containing diethyl carbonate and the ethyl oxitol impurity.

As discussed above, before a dialkyl carbonate is transformed into a valuable end product in any subsequent process, the alkoxy alkanol impurity has to be removed therefrom as that might interfere said subsequent process and/or any further processes. For the above example, this means that the ethyl oxitol impurity should be removed from the bottom stream containing diethyl carbonate and the ethyl oxitol impurity. In principle, ethyl oxitol and diethyl carbonate could be separated by means of a further distillation step. However because of the small difference in boiling point between diethyl carbonate and ethyl oxitol (see above table), such separation is very cumbersome requiring many distillation steps and stages.

Therefore, there is a need to find a simple method of removing an alkoxy alkanol impurity from a dialkyl carbonate stream containing such alkoxy alkanol impurity, and at the same time to prevent a decrease of the overall yield of dialkyl carbonate as much as possible.

SUMMARY OF THE INVENTION

Surprisingly it was found that by contacting the dialkyl carbonate and alkoxy alkanol impurity with a catalyst, a reaction between the dialkyl carbonate and alkoxy alkanol impurity is effected thereby converting the alkoxy alkanol impurity into a compound that can be easily separated from the dialkyl carbonate. In a further step of the present invention, said compound is separated from the dialkyl carbonate resulting in a stream containing said compound and part of the dialkyl carbonate. In addition, according to the present invention, a decrease of the overall yield of dialkyl carbonate is advantageously prevented as much as possible by recycling said stream containing (i) the compound derived from the alkoxy alkanol impurity and (ii) part of the dialkyl carbonate to a distillation column wherein alkanediol is separated from dialkyl carbonate.

Accordingly, the present invention relates to a process for the preparation of an alkanediol and a dialkyl carbonate comprising:
(a) reacting an alkylene carbonate and an alkanol in the presence of a transesterification catalyst to obtain a reaction mixture comprising dialkyl carbonate, unconverted alkanol, alkanediol, unconverted alkylene carbonate and an alkoxy alkanol impurity;
(b) subjecting the reaction mixture to distillation in a first distillation column to obtain a top stream comprising dialkyl carbonate, alkanol and alkoxy alkanol impurity and a bottom stream comprising alkanediol and alkylene carbonate;
(c) subjecting the bottom stream from the first distillation column to distillation in a second distillation column to obtain a top stream comprising alkanediol and a bottom stream comprising alkylene carbonate;
(d) subjecting the top stream from the first distillation column to distillation in a third distillation column in the presence of a catalyst to effect reaction of the alkoxy alkanol impurity with the dialkyl carbonate into a carbonate ether impurity, to obtain a top stream comprising alkanol and a bottom stream comprising dialkyl carbonate and carbonate ether impurity; and
(e) subjecting the bottom stream from the third distillation column to distillation in a fourth distillation column to obtain a top stream comprising dialkyl carbonate and a bottom stream comprising dialkyl carbonate and carbonate ether impurity; and
(f) recycling the bottom stream from the fourth distillation column to the first distillation column.

DETAILED DESCRIPTION OF THE INVENTION

The dialkyl carbonate to be produced in the present invention, may be a di($C_1$-$C_5$)alkyl carbonate, wherein the alkyl groups (straight, branched and/or cyclic) may be the same or different, such as methyl, ethyl and propyl; Specifically, the dialkyl carbonate is diethyl carbonate.

The alkoxy alkanol impurity to be removed in the present invention, may be 2-ethoxyethanol, as described above.

The amount of the alkoxy alkanol impurity in the reaction mixture and in the top stream from the first distillation column may be comprised in the range of from 0.01 to 10 wt. %, specifically 0.02 to 5 wt. %, more specifically 0.03 to 1 wt. % and most specifically 0.05 to 0.5 wt. %.

The reaction of the alkoxy alkanol impurity with the dialkyl carbonate in the presence of a catalyst in accordance with the present invention, results in transesterification of the dialkyl carbonate. Therefore, the catalyst that needs to be used in reacting the alkoxy alkanol impurity with the dialkyl carbonate in the process of the present invention should be a transesterification catalyst. The top stream from the first distillation column comprising dialkyl carbonate, alkanol and alkoxy alkanol impurity does not contain a catalyst. More in particular, said stream does not contain a transesterification catalyst before it is contacted with a catalyst in the third distillation column.

The transesterification catalyst to be used in step (d) of the present process may be one of many suitable homogeneous and heterogeneous transesterification catalysts known from prior art.

For example, suitable homogeneous transesterification catalysts to be used in step (d) of the present process have been described in U.S. Pat. No. 5,359,118 and include hydrides, oxides, hydroxides, alkanolates, amides, or salts of alkali metals, i.e., lithium, sodium, potassium, rubidium and cesium. Preferred homogeneous transesterification catalysts are hydroxides or alkanolates of potassium or sodium. Other suitable homogeneous transesterification catalysts are alkali metal salts, such as acetates, propionates, butyrates, or carbonates. Suitable catalysts are described in U.S. Pat. No. 5,359,118 and the references mentioned therein, such as EP274953A, U.S. Pat. No. 3,803,201, EP1082A, and EP180387A.

As mentioned above, it is also possible to employ a heterogeneous transesterification catalyst in step (d) of the present process. The use of a heterogeneous transesterification catalyst is preferred. Suitable heterogeneous catalysts include ion exchange resins that contain functional groups. Suitable functional groups include tertiary amine groups and quaternary ammonium groups, and also sulphonic acid and carboxylic acid groups. Further suitable catalysts include alkali metal and alkaline earth metal silicates. Suitable catalysts have been disclosed in U.S. Pat. Nos. 4,062,884 and 4,691,041. The heterogeneous catalyst may be selected from ion exchange resins comprising a polystyrene matrix and tertiary amine functional groups. An example is Amberlyst A-21 (ex Rohm & Haas) comprising a polystyrene matrix to which N,N-dimethylamine groups have been attached. Eight classes of transesterification catalysts, including ion exchange resins with tertiary amine and quaternary ammonium groups, are disclosed in J F Knifton et al., J. Mol. Catal, 67 (1991) 389ff.

The heterogeneous transesterification catalyst that may be used in step (d) of the present process may be a catalyst comprising an element from Group 4 (such as titanium), Group 5 (such as vanadium), Group 6 (such as chromium or molybdenum) or Group 12 (such as zinc) of the Periodic Table of the Elements, or tin or lead, or a combination of such elements, such as a combination of zinc with chromium (for example zinc chromite). Said elements may be present in the catalyst as an oxide, such as zinc oxide. Preferably, the transesterification catalyst to be used in step (d) of the present invention is a heterogeneous catalyst comprising zinc.

Further transesterification conditions for step (d) are known in the art and suitably include a temperature from 40 to 200° C., and a pressure from 50 to 5000 kPa (0.5 to 50 bar).

The above-described transesterification catalyst and other transesterification conditions are equally applicable to step (a) of the present process.

In a case where the dialkyl carbonate is a compound of formula $R_1OC(O)OR_2$ wherein $R_1$ and $R_2$ may the same or a different alkyl and the alkoxy alkanol impurity is a compound of formula $R_3OH$ wherein $R_3$ is an alkoxyalkyl group, the following reactions (1) and/or (2) and/or (3) may take place in step (d) of the present process:

$$R_1OC(O)OR_2 + R_3OH \rightarrow R_3OC(O)OR_2 + R_1OH \quad (1)$$

$$R_3OC(O)OR_2 + R_3OH \rightarrow R_3OC(O)OR_3 + R_2OH \quad (2)$$

$$2R_3OC(O)OR_2 \rightarrow R_3OC(O)OR_3 + R_2OC(O)OR_2 \quad (3)$$

In a case where said $R_1OC(O)OR_2$ is diethyl carbonate (or EtOC(O)OEt) and said $R_3OH$ is 2-ethoxyethanol (or EtO-EtOH), the following reactions (1) and/or (2) and/or (3) may take place in the presence of a transesterification catalyst in step (d) of the present process:

$$EtOC(O)OEt + EtOEtOH \rightarrow EtOC(O)OEtOEt + EtOH \quad (1)$$

$$EtOC(O)OEtOEt + EtOEtOH \rightarrow EtOEtOC(O)OEtOEt + EtOH \quad (2)$$

$$2EtOC(O)OEtOEt \rightarrow EtOEtOC(O)OEtOEt + EtOC(O)OEt \quad (3)$$

Said EtOC(O)OEtOEt (OxEC) is a carbonate ether containing 1 ether group, namely ethyl 2-ethoxyethyl carbonate which is a mixed carbonate. EtOEtOC(O)OEtOEt (DOxC) is a carbonate ether containing 2 ether groups, namely di(2-ethoxyethyl)carbonate.

In step (d) of the present process, separation of the dialkyl carbonate from unconverted alkanol is effected by means of distillation in the third distillation column. Such distillation results in a top stream containing unconverted alkanol (such as ethanol), which may be recycled, partially or completely, to step (a) of the present process, and a bottom stream containing dialkyl carbonate (such as diethyl carbonate). Further, in step (d) of the present process, the catalyst for effecting reaction of the alkoxy alkanol impurity with the dialkyl carbonate may be added to the third distillation column itself or to a reactor of which the inlet and outlet are connected to said third distillation column.

In a case where in step (d) of the present process, the catalyst is added to the third distillation column itself, said addition preferably takes place at a position where the concentration of unconverted alkanol (such as ethanol) is relatively low (for example 0 to 0.5 wt. %) so that reaction of the dialkyl carbonate (such as diethyl carbonate) with the alkoxy alkanol impurity (such as 2-ethoxyethanol) is favoured in case the latter reaction would result in the production of an alkanol (such as ethanol) which is the same as the unconverted alkanol. For example, the catalyst may be added to the stripping section of the third distillation column and/or to the reboiler section at the bottom of the third distillation column.

In a case where in step (d) of the present process, the catalyst is added to a reactor of which the inlet and outlet are connected to said third distillation column, said inlet is preferably connected to said column at a position where the concentration of unconverted alkanol in the column is relatively low, for the same reasons as described for the case where the catalyst is added to the third distillation column itself.

In all of these cases, where the alkanol resulting from reaction of the dialkyl carbonate with the alkoxy alkanol impurity is the same as the unconverted alkanol, the newly formed alkanol is favourably removed overhead together with the unconverted alkanol as part of the top stream from the third distillation column. There is question of reactive distillation. This alkanol removal has the additional advantage of shifting the equilibrium of the reaction of the dialkyl carbonate with the alkoxy alkanol impurity into the desired direction.

The present invention advantageously results in the removal of an alkoxy alkanol impurity in dialkyl carbonate streams, which alkoxy alkanol impurity might have interfered in any subsequent process using said dialkyl carbonate if it would not have been removed. It is recognised that by doing this said alkoxy alkanol impurity and part of the dialkyl carbonate is converted into another carbonate(s), namely carbonate ether impurity.

However, said carbonate ether impurity may easily be separated from the bottom stream from the third distillation column comprising dialkyl carbonate and carbonate ether impurity, resulting in pure dialkyl carbonate. Therefore, the present process comprises the additional step (e) of subjecting the bottom stream from the third distillation column to distillation in a fourth distillation column to obtain a top stream comprising dialkyl carbonate and a bottom stream comprising dialkyl carbonate and carbonate ether impurity.

Said carbonate ether impurity may be the product directly resulting from the reaction of the alkoxy alkanol impurity with the dialkyl carbonate, or the product(s) resulting from any of the above further reactions (2) and (3). Optionally, step (e) of the present process is performed in the presence of a transesterification catalyst in the fourth distillation column so that above-mentioned reaction (3) may take place and/or may be completed resulting in recovery of part of the dialkyl carbonate that had reacted with the alkoxy alkanol impurity before.

For example, in a case where a stream containing diethyl carbonate and 2-ethoxyethanol impurity has been contacted with a transesterification catalyst in step (d) of the present process, pure diethyl carbonate may easily be obtained by means of distillation in (e) of the present process, in view of the boiling point differences between diethyl carbonate and the resultant carbonate ether products. This is indicated in the table below.

| Component | Boiling point (° C.) |
|---|---|
| ethanol | 78.4 |
| diethyl carbonate | 126-128 |
| ethyl 2-ethoxyethyl carbonate | 190.2 (*) |
| di(2-ethoxyethyl) carbonate | 245.5 (*) |

(*) Calculated using ACD/Labs Software V9.04 from Solaris ( ©1994-2008 ACD/Labs)

The bottom stream from the fourth distillation column obtained in step (e) of the present process comprises dialkyl carbonate and carbonate ether impurity. In addition, said stream may comprise some alkanediol. By removing said stream from the process, the carbonate ether impurity would indeed advantageously be bled from the process. However, by doing that, valuable dialkyl carbonate and optionally valuable alkanediol as comprised in said stream would also be removed, thereby reducing the overall yield of said product(s). Therefore, the present process advantageously comprises the additional step (f) of recycling the bottom stream from the fourth distillation column to the first distillation column. In this way, additional dialkyl carbonate, and optionally additional alkanediol, is yielded by subjecting, in step (b), the reaction mixture obtained in step (a), in combination with the recycled bottom stream from the fourth distillation column obtained in step (e), to distillation in the first distillation column to obtain a top stream comprising dialkyl carbonate, alkanol and alkoxy alkanol impurity and a bottom stream comprising alkanediol, alkylene carbonate and carbonate ether impurity.

Further, said bottom stream from the first distillation column comprising alkanediol, alkylene carbonate and carbonate ether impurity is subjected, in step (c), to distillation in the second distillation column to obtain a top stream comprising alkanediol and carbonate ether impurity and a bottom stream comprising alkylene carbonate. Said bottom stream comprising alkylene carbonate may also comprise carbonate ether impurity, more especially a carbonate ether containing 2 ether groups. The bottom stream comprising alkylene carbonate may be recycled, partially or completely, to step (a) of the present process. Further, said top stream comprising alkanediol and carbonate ether impurity may comprise some alkylene carbonate. In order to further purify the alkanediol, the present process preferably comprises additionally:

(g) subjecting the top stream from the second distillation column to hydrolysis, preferably in the presence of a hydrolysis catalyst.

Such hydrolysis is advantageous in that the carbonate ether impurity will be hydrolysed into components that can be easily separated from the alkanediol, so as to prepare pure alkanediol. For example, where the carbonate ether impurity comprises ethyl 2-ethoxyethyl carbonate (EtOC(O)OEtOEt), hydrolysis will result in formation of 2-ethoxyethanol, carbon dioxide and ethanol which all can be easily separated from monoethylene glycol, for example by means of distillation. In a case where the top stream from the second distillation column also comprises some alkylene carbonate, such alkylene carbonate will also be hydrolysed in step (g) yielding carbon dioxide and additional alkanediol.

Still further, part of the bottom stream from the second distillation column may be subjected to hydrolysis, preferably in the presence of a hydrolysis catalyst and preferably in combination with the top stream from the second distillation column, whereas the remainder of said bottom stream is recycled to step (a) of the present process. In a case where said bottom stream comprises carbonate ether impurity, this ensures that no build-up of carbonate ether impurity can occur. In respect of subjecting, partially or completely, the top and/or bottom streams from a distillation column similar to the second distillation column in the present process, to hydrolysis, more in particular in respect of the hydrolysis catalyst, hydrolysis conditions and further work-up procedure to yield pure alkanediol, that may be used, reference is made to above-mentioned WO2008090108, the contents of which is herein incorporated by reference.

In FIG. 1 a flow scheme for the process according to the present invention is shown. Although the process will be described for ethanol as a suitable alcohol and ethylene carbonate as the alkylene carbonate the skilled person will understand that other alkanols and alkylene carbonates can be similarly used.

Ethanol is passed via a line 1 into a reactor 2. Reactor 2 can suitably be a continuously stirred tank reactor or a plug flow reactor. Via a line 3 ethylene carbonate is also fed into reactor 2. A transesterification catalyst is present in reactor 2, which catalyst may be fed continuously to said reactor. The catalyst may be mixed with the reactants in line 1 or line 3 or fed to the reactor 2 via a separate line (not shown).

Via a line 4, the reaction mixture from reactor 2, comprising diethyl carbonate, unconverted ethanol, monoethylene glycol, unconverted ethylene carbonate and 2-ethoxyethanol impurity, is fed into a distillation column 5. In distillation column 5, said mixture is separated into a top fraction comprising diethyl carbonate, ethanol and 2-ethoxyethanol impurity that is withdrawn via a line 6, and a bottom fraction comprising monoethylene glycol and ethylene carbonate that is withdrawn via a line 7.

The top stream from distillation column 5 is sent to a distillation column 8, where separation into ethanol and diethyl carbonate is performed in the presence of a transesterification catalyst to effect reaction of the 2-ethoxyethanol impurity with the dialkyl carbonate into a carbonate ether impurity, comprising ethyl 2-ethoxyethyl carbonate and possibly di(2-ethoxyethyl)carbonate, to obtain a top stream comprising alkanol and a bottom stream comprising dialkyl carbonate and carbonate ether impurity.

Ethanol is recovered from distillation column 8 via a line 10 and via line 1 recycled to reactor 2. The bottom stream from distillation column 8 is subjected to a distillation in a distillation column 14. The diethyl carbonate is discharged via a line 15 and recovered as product, optionally after further purification.

The bottom stream from distillation column 14 comprising dialkyl carbonate and carbonate ether impurity is recycled to distillation column 5 via line 16. Alternatively, said recycling may be performed via lines 16 and 4 consecutively (not shown).

The bottom stream from distillation column 5 in line 7, which stream in addition to monoethylene glycol and ethylene carbonate comprises carbonate ether impurity, is subjected to distillation in a distillation column 11. In distillation column 11 a top product comprising monoethylene glycol and carbonate ether impurity is withdrawn via line 12. Since said top product is contaminated with carbonate ether impurity, and possibly with some ethylene carbonate, further purification may be considered including hydrolysis as discussed above (not shown in FIG. 1).

Further, a bottom stream comprising ethylene carbonate is withdrawn from distillation column 11 via line 13, which stream is partially or completely recycled, optionally after further purification, to reactor 2 via line 3.

In summary, in the present invention, an unwanted impurity, that is to say an alkoxy alkanol impurity, is converted into a compound that can be easily separated from the dialkyl carbonate containing said alkoxy alkanol impurity. An additional step is needed for separating the dialkyl carbonate from the newly formed contaminant, that is to say a carbonate ether impurity, so as to obtain pure dialkyl carbonate. Such additional separation could result in loss of some dialkyl carbonate. However, by recycling the stream containing the dialkyl carbonate and the carbonate ether impurity into the process, a decrease of the overall yield of dialkyl carbonate is prevented as much as possible.

Further, the present invention relates to a process for making a diaryl carbonate, comprising contacting, in the presence of a transesterification catalyst, an aryl alcohol with a stream containing a dialkyl carbonate from which stream an alkoxy alkanol impurity has been removed in accordance with the above-mentioned process.

Still further, the present invention relates to a process for making a diaryl carbonate, comprising steps (a) to (f) of the above-mentioned process and additionally comprising:

(h) contacting, in the presence of a transesterification catalyst, an aryl alcohol with the top stream comprising dialkyl carbonate from the fourth distillation column.

Preferably, said diaryl carbonate is diphenyl carbonate and said aryl alcohol is phenol.

The above-described transesterification catalyst and other transesterification conditions are equally applicable to said process for making a diaryl carbonate.

The invention is further illustrated by the following Example.

EXAMPLE 30 g of diethyl carbonate (DEC), containing 0.8 wt. % of ethyl oxitol (EtOEtOH; 2-ethoxyethanol), and 6.08 g of a heterogeneous catalyst comprising zinc were placed in a round bottom flask under nitrogen. The resulting suspension was stirred under atmospheric pressure with a magnetic stirrer and heated at 100° C. with an oil bath, for 235 minutes. The catalyst was ZN-0312 T 1/8 (HT) catalyst supplied by BASF, which is a mixture of zinc oxide (about 65 wt. %) and zinc chromite (about 35 wt. %).

A condenser was fitted to the flask to keep any light components in the reaction mixture. At the start and at the end of the experiment, samples of the reaction mixture were taken and analyzed using GC chromatography. The analysis results are indicated in the Table below.

| Components | Amount (wt. %) at start | Amount (wt. %) at end |
|---|---|---|
| EtOC(O)OEt (DEC) | 99.2 | 98.0 |
| EtOEtOH (ethyl oxitol) | 0.8 | 0 |
| EtOC(O)OEtOEt | 0 | 1.9 |
| EtOEtOC(O)OEtOEt | 0 | trace |

From the results in the above table it appears that the 2-ethoxyethanol contaminant was quantitatively converted into ethyl 2-ethoxyethyl carbonate and a trace amount of di(2-ethoxyethyl)carbonate. The differences in boiling point between DEC and ethyl 2-ethoxyethyl carbonate and between DEC and di(2-ethoxyethyl)carbonate are such (see the 2nd table in the description preceding this Example) that said higher boiling carbonates can be easily removed from DEC, resulting in pure DEC.

What is claimed is:

1. A process for the preparation of an alkanediol and a dialkyl carbonate comprising:
   (a) reacting an alkylene carbonate and an alkanol in the presence of a transesterification catalyst to obtain a reaction mixture comprising dialkyl carbonate, unconverted alkanol, alkanediol, unconverted alkylene carbonate and an alkoxy alkanol impurity;
   (b) subjecting the reaction mixture to distillation in a first distillation column to obtain a top stream comprising dialkyl carbonate, alkanol and alkoxy alkanol impurity and a bottom stream comprising alkanediol and alkylene carbonate;
   (c) subjecting the bottom stream from the first distillation column to distillation in a second distillation column to obtain a top stream comprising alkanediol and a bottom stream comprising alkylene carbonate;
   (d) subjecting the top stream from the first distillation column to distillation in a third distillation column in the presence of a catalyst to effect reaction of the alkoxy alkanol impurity with the dialkyl carbonate into a carbonate ether impurity, to obtain a top stream comprising alkanol and a bottom stream comprising dialkyl carbonate and carbonate ether impurity; and
   (e) subjecting the bottom stream from the third distillation column to distillation in a fourth distillation column to obtain a top stream comprising dialkyl carbonate and a bottom stream comprising dialkyl carbonate and carbonate ether impurity; and
   (f) recycling the bottom stream from the fourth distillation column to the first distillation column.

2. A process according to claim 1, wherein the dialkyl carbonate is a di($C_1$-$C_5$)alkyl carbonate.

3. A process according to claim 1, wherein the catalyst in step (d) is a heterogeneous catalyst.

4. A process according to claim 1, wherein the alkylene carbonate is ethylene carbonate, the unconverted alkanol is ethanol, the dialkyl carbonate is diethyl carbonate, the alkanediol is monoethylene glycol and the alkoxy alkanol impurity is 2-ethoxyethanol.

5. A process for making a diaryl carbonate, comprising
   (a) reacting an alkylene carbonate and an alkanol in the presence of a transesterification catalyst to obtain a reaction mixture comprising dialkyl carbonate, unconverted alkanol, alkanediol, unconverted alkylene carbonate and an alkoxy alkanol impurity;
   (b) subjecting the reaction mixture to distillation in a first distillation column to obtain a top stream comprising dialkyl carbonate, alkanol and alkoxy alkanol impurity and a bottom stream comprising alkanediol and alkylene carbonate;
   (c) subjecting the bottom stream from the first distillation column to distillation in a second distillation column to obtain a top stream comprising alkanediol and a bottom stream comprising alkylene carbonate;
   (d) subjecting the top stream from the first distillation column to distillation in a third distillation column in the presence of a catalyst to effect reaction of the alkoxy alkanol impurity with the dialkyl carbonate into a carbonate ether impurity, to obtain a top stream comprising alkanol and a bottom stream comprising dialkyl carbonate and carbonate ether impurity; and
   (e) subjecting the bottom stream from the third distillation column to distillation in a fourth distillation column to obtain a top stream comprising dialkyl carbonate and a bottom stream comprising dialkyl carbonate and carbonate ether impurity; and
   (f) recycling the bottom stream from the fourth distillation column to the first distillation column;
   and additionally comprising: (h) contacting, in the presence of a transesterification catalyst, an aryl alcohol with the top stream comprising dialkyl carbonate from the fourth distillation column.

6. A process according to claim 5, wherein the diaryl carbonate is diphenyl carbonate and the aryl alcohol is phenol.

* * * * *